United States Patent [19]

Katsumata et al.

[11] Patent Number: 5,478,733

[45] Date of Patent: Dec. 26, 1995

[54] PROCESS FOR PRODUCING L-ALANINE BY FERMENTATION WITH ARTHROBACTER

[75] Inventors: Ryoichi Katsumata; Shinichi Hashimoto, both of Tokyo; Isao Kawamoto, Hiratsuka; Makoto Suzuki, Tokyo; Hajime Yoshida, Sagamihara; Hiroshi Hagino, Tokyo; Kiyoshi Nakayama, Sagamihara, all of Japan

[73] Assignee: Kyowa Hakko Kogyo Co., Ltd., Tokyo, Japan

[21] Appl. No.: 90,198

[22] Filed: Jul. 16, 1993

[51] Int. Cl.$^6$ ............... C12N 1/20; C12P 13/06
[52] U.S. Cl. ............. 435/116; 435/252.1; 435/830
[58] Field of Search ............... 435/116, 830, 435/252.1

[56] References Cited

U.S. PATENT DOCUMENTS

| | | | |
|---|---|---|---|
| 3,458,400 | 7/1969 | Chibata et al. | 195/29 |
| 5,100,782 | 3/1992 | Klages et al. | 435/42 |
| 5,124,257 | 6/1992 | Azizian et al. | 435/116 |
| 5,130,240 | 7/1992 | Ozaki et al. | 435/116 |
| 5,252,470 | 10/1993 | Ozaki et al. | 435/116 |

FOREIGN PATENT DOCUMENTS

| | | |
|---|---|---|
| 57-132882 | 8/1982 | Japan . |
| 62-087088 | 4/1987 | Japan . |
| 4330291 | 11/1992 | Japan . |

OTHER PUBLICATIONS

Hashimoto et al, Biotech. Letters, 15(11):1117–1122, (Nov. 1993).

*Primary Examiner*—Marian C. Knode
*Assistant Examiner*—Deborah K. Ware
*Attorney, Agent, or Firm*—Antonelli, Terry, Stout & Kraus

[57] ABSTRACT

A process for producing L-alanine, which comprises culturing in a medium a microorganism belonging to the genus Arthrobacter which has L-alanine dehydrogenase activity, but little or no alanine racemase activity, and which is capable of producing L-alanine; allowing L-alanine to accumulate in the culture; and recovering L-alanine from the culture.

1 Claim, No Drawings

PROCESS FOR PRODUCING L-ALANINE BY FERMENTATION WITH ARTHROBACTER

This application is a 371 of PCT/JP91/01574 filed Nov. 18, 1991.

TECHNICAL FIELD

The present invention relates to a process for producing L-alanine which is an amino acid constituting the living body and is useful as a nutrient infusion, a medicament and a food additive.

BACKGROUND ART

Heretofore, for the production of L-alanine, a process in which L-aspartic acid is subjected to enzymatic decarboxylation (Japanese Published Examined Patent Application No. 7560/1971), a process in which fumaric acid is led to L-aspartic acid which is then subjected to enzymatic decarboxylation (Japanese Published Unexamined Patent Application No. 268691/1990), etc. have been employed. There are also known a process for producing L-alanine from lactic acid and an ammonia donor by using D-alanine-requiring *E. coli* (Japanese Published Unexamined Patent Application No. 36196/1987), a fermentation process with *Corynebacterium tumescens* using a carbohydrate (Japanese Published Examined Patent Application No. 14298/1961), etc.

The known processes for producing L-alanine by fermentation are disadvantageous in that the amounts of the product accumulated in the culture broth are small, the yields are low, the production rates are low, the culturing requires a long time, and so on. Therefore, these processes are little practical in the industrial production of L-alanine. Also a report has been made on fermentation production of D,L-alanine in high yields (Japanese Published Examined Patent Application No. 797/1982). However, this process is not industrially advantageous because the produced alanine is a racemic mixture of D- and L-forms, thereby necessitating a step of optical resolution of the D- and L-forms in order to obtain L-alanine.

DISCLOSURE OF THE INVENTION

According to the present invention, there is provided a process for producing L-alanine, which comprises culturing in a nutrient culture medium a microorganism belonging to the genus Arthrobacter which has L-alanine dehydrogenase activity, but little or no alanine racemase activity, and which is capable of producing L-alanine; allowing L-alanine to accumulate in the culture; and recovering L-alanine from the culture.

The present invention is described in detail below.

In the present invention, any microorganism belonging to the genus Arthrobacter may be used as long as it has L-alanine dehydrogenase activity, but little or no alanine racemase activity, and is capable of producing L-alanine. Such microorganisms can be induced from microorganisms which belong to the genus Arthrobacter and have L-alanine dehydrogenase activity and L-alanine productivity as parent strains. Examples of the parent strains of the microorganisms which may be used in the present invention include Arthrobacter sp. HAP1 (FERM BP-3644), *Arthrobacter ureafaciens* ATCC 7562 and *Arthrobacter histidinolovorans* ATCC 11442.

Arthrobacter sp. HAP1 strain (FERM BP-3644) is a strain which was first isolated by the present inventors from a soil sample obtained in Machida City, whose bacteriological properties are described in detail below.

(a) Morphology (1) Shape and size of the cells: rod-like or spherical polymorph (diameter: 1.0–2.0 μm, length: 1.0–4.0 μm or more)
(2) Motility: −
(3) Spore: no formation
(4) Gram stain: positive
(5) Acid-fastness: negative (b) Growth on various culture media (1) Broth agar plate culture: an ivory smooth colony is formed, without formation of a diffusible pigment
(2) Broth agar slant culture: full growth
(3) Broth liquid culture: growth to cause turbidity, without surface growth
(4) Broth gelatine stab culture: growth observed, without liquefaction of gelatine
(5) Litmus milk: litmus is reduced, and milk is liquefied (c) Physiological properties (1) Reduction of nitrate: positive
(2) Denitrification reaction: negative
(3) MR test: negative
(4) VP test: negative
(5) Formation of indole: negative
(6) Formation of hydrogen sulfide: negative
(7) Hydrolysis of starch: positive
(8) Utilization of citric acid: (Koser) positive, (Christensen) positive
(9) Utilization of inorganic nitrogen: nitrate (positive), ammonium salt (positive)
(10) Formation of pigment: negative
(11) Urease: positive
(12) Oxidase: negative
(13) Catalase: positive
(14) Growth range:
  1) pH: 5.1–10.0
  2) Temperature: 7°–38° C.
(15) Oxygen demand: aerobic
(16) O–F test: oxidation
(17) Formation of acid and gas from saccharides

|  | Formation of acid | | Formation of gas | |
| --- | --- | --- | --- | --- |
|  | aerobic | anaerobic | aerobic | anaerobic |
| L-arabinose | − |  | − |  |
| D-xylose | − | − | − | − |
| D-glucose | − | − | − | − |
| D-mannose | − |  | − |  |
| D-fructose | − |  | − |  |
| D-galactose | − | − | − | − |
| Maltose | − |  | − |  |
| Sucrose | − |  | − |  |
| Lactose | − |  | − |  |
| Trehalose | − |  | − |  |
| D-sorbitol | − |  | − |  |
| D-mannitol | − |  | − |  |
| Inositol | − |  | − |  |
| Glycerine | − |  | − |  |
| Starch | − |  | − |  |

(d) Other Properties (1) Assimilability of carbon compounds

Assimilable: p-hydroxybenzoate, glyoxylic acid, L-asparagine, L-arginine, L-histidine, D-xylose, D-ribose, D-galactose, L-rhamnose and glycerol Non-assimilable: D-arabinose (2) Amino acid composition of cell wall: lysine, alanine, glutamic acid, threonine, serine and glycine (3) Major quinone: 1-saturated type of menaquinone-9 [MK-9($H_2$)]

A search was made through Bergey's Manual of Systematic Bacteriology for a strain having the bacteriological properties described above, and it was concluded that the above strain belongs to Section 15 (Irregular, Nonsporing, Gram-Positive Rods) in Vol. 2 (1986) in view of the facts that it is a gram-positive, and rod-like or spherical polymorph. A further search was made on the basis of the facts that it grows under aerobic conditions, but not under anaerobic conditions, the amino acid composition of its cell wall comprises lysine, threonine and serine, and it includes MK-9($H_2$) as a major quinone. As a result, the above strain was identified as a bacterium which belongs to the genus Arthrobacter. The HAP1 strain was named Arthrobacter sp. HAP1 and was deposited with the Fermentation Research Institute, Agency of Industrial Science and Technology (FRI) on Nov. 7, 1991 under the Budapest Treaty, as FERM BP-3644.

The microorganism with little or no alanine racemase activity used in the present invention can be isolated by subjecting a wild strain having the alanine racemase activity to mutagenesis such as ultraviolet irradiation or chemical treatment with N-methyl-N'-nitro-N-nitrosoguanidine (hereinafter abbreviated to NTG), nitrous acid or the like, and then selecting a strain which fails to grow or grows at a lower rate than its parent strain on a D-alanine-free culture medium. Representative examples of the thus obtained strains include LAP7 strain induced from Arthrobacter sp. HAP1 strain, and AU-7 strain induced form *Arthrobacter ureafaciens* ATCC 7562 strain. The LAP7 strain and the AU-7 strain were deposited together with the HAP1 strain with the Fermentation Research Institute, Agency of Industrial Science and Technology on Nov. 7, 1991 under the Budapest Treaty, as FERM BP-3645 and FERM BP-3646, respectively.

The production of L-alanine by the microorganism of the present invention may be carried out by a method conventionally used for the culturing of microorganisms. As the culture medium, any of synthetic or natural media can be used so far as it appropriately contains a carbon source, a nitrogen source, inorganic substances, an appropriate amount of D-alanine or D,L-alanine, and trace amounts of other nutrients which the strain used requires.

Any carbon source may be used so far as it is assimilated by the microorganism used. Examples of suitable carbon sources are carbohydrates such as glucose, glycerol, fructose, sucrose, starch hydrolyzate and molasses, and organic acids such as pyruvic acid, succinic acid and lactic acid.

As the nitrogen source, ammonia; various inorganic or organic ammonium salts such as ammonium chloride, ammonium sulfate, ammonium carbonate, ammonium acetate and urea; and natural nutrients such as peptone, NZ-amine, meat extract, yeast extract, corn steep liquor and casein hydrolyzate may be used.

As the inorganic substance, potassium dihydrogenphosphate, dipotassium hydrogenphosphate, magnesium sulfate, sodium chloride, ferrous sulfate, manganese sulfate, zinc sulfate, calcium chloride, and the like may be added.

Further, vitamins such as biotin and thiamine may be added if necessary.

Generally, it is preferred to carry out the culturing at a temperature of 20°–40° C. The pH of the culture medium is desirably kept in a neutral range. The carbon source, nitrogen source and other nutrients may be added at once at the start of the culturing or in several portions or continuously during the culturing, provided that the growth of the microorganism is not inhibited. The culturing period varies depending on the amounts of the carbon source, nitrogen source and other nutrients added, but is usually 1–6 days.

After the completion of the culturing, L-alanine can be isolated by removing the cells from the culture and then subjecting the resulting cell-free culture liquor to a known purification process such as crystallization by concentration or treatment with activated carbon or an ion exchange resin.

Best Mode for Carrying Out the Invention

Example 1

Arthrobacter sp. HAP1 strain was cultured in a complete medium (a medium which contains 20 g of powdered bouillon and 5 g of yeast extract in 1 liter of water and is adjusted to pH 7.2) at 30° C. for 16 hours. The cells were collected, washed with a 0.05M Tris-maleate buffer solution (pH 6.0), and then suspended in the same buffer solution to a cell concentration of about $10^9$ cells/ml. To the suspension was added NTG to a final concentration of 500 mg/l, and the mixture was kept at 30° C. for 20 minutes for mutagenic treatment. The treated cells were washed with the same buffer solution as used above, and then smeared on a minimum agar plate medium (Table 1) containing 0.05 g/l D-alanine.

TABLE 1

| Composition of minimum medium | |
|---|---|
| Glucose | 5 g/l |
| $(NH_4)_2SO_4$ | 5 g/l |
| $MgSO_4.7H_2O$ | 0.5 g/l |
| $NH_4Cl$ | 3 g/l |
| $KH_2PO_4$ | 3 g/l |
| $FeSO_4.7H_2O$ | 10 mg/l |
| $MnSO_4.6H_2O$ | 2 mg/l |
| Biotin | 30 μg/l |
| Thiamine hydrochloride | 0.5 mg/l |
| Agar | 20 g/l (pH 7.2) |

Culturing was carried out at 30° C. for 2–4 days, and the colonies growing on said plate were applied on a minimum agar medium containing D-alanine (0.05 g/l) and a minimum agar medium lacking D-alanine. Strains which grew on the former medium in the same manner as the parent strain, but failed to grow or grew at lower rates than the parent strain on the latter medium were picked up. Of the thus selected mutants, Arthrobacter sp. LAP7 strain was obtained as a strain with alanine racemase activity lowered or deleted. In Table 3 are shown the alanine racemase activities of the parent HAP1 strain and the mutant LAP7 strain.

The determination of alanine racemase activity was carried out by the method of Wijsman, H. J. W. [Genet. Res., Camb. 20: 269–277 (1972)], and the determination of L-alanine dehydrogenase activity was carried out according to the method of Ohosima, T. et al. [Eur. J. Biochem., 100: 29–39 (1979)].

Example 2

The mutant Arthrobacter sp. LAP7 strain obtained in the preceding example and its parent strain HAP1 were inoculated into 10 ml of a seed culture medium (2% glucose, 1% peptone, 1% yeast extract, 0.5% NaCl, 200 mg/l D-alanine, pH 7.2) in a test tube, and subjected to shaking culture at 30° C. for 24 hours. The resulting seed culture (1 ml) was inoculated into 20 ml of a fermentation medium shown in Table 2 in a 300-ml Erlenmeyer flask, and subjected to shaking culture at 30° C. for 48 hours. After the culturing, the filtrate of the culture was subjected to high performance liquid chromatography using LiChrosorb RP-18 column (7 μm) manufactured by Merck & Co., Inc., and the quantitative determination of the total alanine (T-Ala) was made by the post column color development method with ophthalaldehyde. D-alanine was determined by a method using commercially available D-amino acid oxidase (Boehringer Mannheim Yamanouchi, Inc.) and by high performance liquid chromatography (HPLC) using Crown Pack column manufactured by DAICEL CHEMICAL INDUSTRIES, LTD. The results are shown in Table 3.

TABLE 2

| Composition of fermentation medium | |
| --- | --- |
| Glucose | 8% |
| Ammonium sulfate | 3% |
| Potassium dihydrogenphosphate | 0.1% |
| Magnesium sulfate | 0.5% |
| Manganese sulfate | 5 mg/l |
| Zinc sulfate | 10 mg/l |
| Biotin | 30 μg/l |
| D-alanine | 200 mg/l (pH 7.2) |

TABLE 3

| Strain | Enzyme activity (%)*[1] | | Amount of D,L-alanine accumulated (g/l) | L/L + D (%)*[2] |
| --- | --- | --- | --- | --- |
| | Alanine racemase | L-alanine dehydrogenase | | |
| HAP1 | 100 | 100 | 18.5 | 58 |
| LAP7 | 1 | 100 | 20.0 | 98 |

*[1]Relative value with the specific activity of the parent strain defined as 100%.
*[2]L/L + D = [(amount of D,L-alanine) − (amount of D-alanine)]/(amount of D,L-alanine) × 100

Example 3

*Arthrobacter ureafaciens* ATCC 7562 was subjected to mutagenic treatment in the same manner as in Example 1, and strains which grew on the D-alanine-containing minimum agar plate medium (Table 1) in the same manner as the parent strain, but failed to grow or grew at lower rates than the parent strain on the D-alanine-lacking minimum agar plate medium were picked up. Of the thus selected mutants, *Arthrobacter ureafaciens* AU-7 strain with alanine racemase activity lowered or deleted was obtained. In Table 4 are shown the alanine racemase activities of the parent strain ATCC 7562 and the mutant AU-7 strain.

Example 4

The mutant *Arthrobacter ureafaciens* AU-7 strain obtained in the preceding example and its parent strain ATCC 7562 were cultured in the same manner as in Example 2, and the filtrate of the culture was analyzed in the same manner as in Example 2. The results are shown in Table 4.

TABLE 4

| Strain | Enzyme activity (%)*[1] | | Amount of D,L-alanine accumulated (g/l) | L/L + D (%)*[2] |
| --- | --- | --- | --- | --- |
| | Alanine racemase | L-alanine dehydrogenase | | |
| ATCC 7562 | 100 | 100 | 10.4 | 55 |
| AU-7 | 1 | 100 | 9.1 | 99 |

*[1]Relative value with the specific activity of the parent strain defined as 100%.
*[2]L/L + D = [(amount of D,L-alanine) − (amount of D-alanine)]/(amount of D,L-alanine) × 100

Example 5

The LAP7 strain was inoculated into 10 ml of a seed culture medium (2% glucose, 1% peptone, 1% yeast extract, 0.5% NaCl, 200 mg/l D-alanine, pH 7.2) in a test tube, and subjected to shaking culture at 30° C. for 24 hours. The resulting seed culture (5 ml) was inoculated into 50 ml of a medium comprising 4% glucose, 1% corn steep liquor, 0.5% peptone, 3% ammonium sulfate, 0.1% potassium dihydrogenphosphate, 0.05% magnesium sulfate, 5 mg/l manganese sulfate, 10 mg/l zinc sulfate, 30 μg/l biotin, 200 mg/l D-alanine and 2% calcium carbonate (pH 7.2) in a 2-liter Erlenmeyer flask. Culturing was carried out with shaking at 30° C. for 24 hours. The whole of the resulting culture was inoculated into a 5-liter jar fermenter containing 1.83 liter of a medium comprising 5% glucose, 3% ammonium sulfate, 0.08% potassium dihydrogenphosphate, 0.07% magnesium sulfate, 7.2 mg/l manganese sulfate, 7.2 mg/l ferrous sulfate, 14.4 mg/l zinc sulfate, 36 μg/l biotin and 1 g/l D-alanine (pH 7.2) and sterilized by heating. Culturing was carried out with aeration and stirring at 30° C. and at a pH kept at 6.5 with ammonia. When the residual glucose reduced to 0.1% or less, continuous addition of a separately sterilized glucose solution to the culture was started, and the culturing was continued until the amount of the charged glucose reached 14%. When the culturing was completed, the L-alanine and D-alanine contents in the filtrate of the culture were 76.7 g/l and 4.4 g/l, respectively (L/D+L=94.6%), and the yield of L-alanine was found to be corresponding to 46.2% of the amount of the charged glucose.

Example 6

The cells were removed by centrifugation from 1 liter of the culture obtained in Example 5, and the resulting supernatant was treated with decolorizing carbon. The decolorizing carbon-treated solution was passed through a column packed with a cation exchange resin, Diaion SK-1B (H+ type), to adsorb L-alanine thereon, followed by washing with water and elution with 2N aqueous ammonia. The L-alanine fraction was concentrated and ethanol was added to the concentrate. The precipitated crystals were collected and recrystallized from ethanol to give 57.7 g of crystals of L-alanine.

Industrial Applicability

According to the present invention, L-alanine which is useful as a nutrient infusion, a medicament and a food additive can be produced by an industrially advantageous process.

We claim:
1. A process for the production of L-alanine, comprising culturing in a nutrient culture medium a microorganism selected from the group consisting of Arthrobacter sp. LAP7 FERM BP-3645 and *Arthrobacter ureafaciens* AU-7 FERM BP-3646; allowing L-alanine to accumulate in the culture; and recovering L-alanine from the culture.

* * * * *